(12) United States Patent
Takei et al.

(10) Patent No.: US 11,087,465 B2
(45) Date of Patent: Aug. 10, 2021

(54) MEDICAL IMAGE PROCESSING APPARATUS, MEDICAL IMAGE PROCESSING METHOD, AND MEDICAL IMAGE PROCESSING PROGRAM

(71) Applicant: FUJIFILM Corporation, Tokyo (JP)

(72) Inventors: Mizuki Takei, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 70 days.

(21) Appl. No.: 16/553,636

(22) Filed: Aug. 28, 2019

(65) Prior Publication Data

US 2020/0090328 A1 Mar. 19, 2020

(30) Foreign Application Priority Data

Sep. 14, 2018 (JP) .............................. JP2018-172988

(51) Int. Cl.
*G06T 7/00* (2017.01)
*G16H 30/20* (2018.01)
(Continued)

(52) U.S. Cl.
CPC .......... *G06T 7/0012* (2013.01); *A61B 5/0042* (2013.01); *A61B 6/501* (2013.01); *G06T 7/11* (2017.01); *G16H 30/20* (2018.01); *G16H 30/40* (2018.01); *A61B 5/055* (2013.01); *A61B 6/032* (2013.01); *A61B 2576/026* (2013.01);
(Continued)

(58) Field of Classification Search
CPC .......... G06T 7/0012; G06T 7/11; G06T 7/68; G06T 2207/10116; G06T 2207/10088; G06T 7/337; G06T 2207/20081; G06T 2207/20076; G06T 2207/10081; G06T 2207/30016; G06T 2207/10104; G16H 30/20; G16H 30/40; G16H 50/20; A61B 6/501; A61B 5/0042; A61B 6/032; A61B 5/055; A61B 2576/026; A61B 5/7264; A61B 5/0261; G06N 20/00; G06N 3/0445;
(Continued)

(56) References Cited

U.S. PATENT DOCUMENTS

2008/0124746 A1* 5/2008 Tang ........................ C12Q 1/18
435/7.32
2009/0028403 A1* 1/2009 Bar-Aviv ............... G16H 50/20
382/128

(Continued)

FOREIGN PATENT DOCUMENTS

JP 2018-011958 A 1/2018

*Primary Examiner* — Kim Y Vu
*Assistant Examiner* — Molly Delaney
(74) *Attorney, Agent, or Firm* — Studebaker & Brackett PC

(57) ABSTRACT

A determination processing unit determines a disease region in a medical image including an axisymmetric structure. A first determination section of the determination processing unit generates a feature amount map of the medical image from the medical image. A second determination section second inverts the feature amount map with reference to a symmetry axis to generate an inverted feature amount map. A third determination section superimposes the feature amount map and the inverted feature amount map on each other and determines the disease region in the medical image using the feature amount map and the inverted feature amount map superimposed on each other.

7 Claims, 6 Drawing Sheets

(51) Int. Cl.
*G06T 7/11* (2017.01)
*A61B 6/00* (2006.01)
*G16H 30/40* (2018.01)
*A61B 5/00* (2006.01)
*A61B 6/03* (2006.01)
*A61B 5/055* (2006.01)
*G06T 7/68* (2017.01)
*G06N 20/00* (2019.01)
*G06T 7/33* (2017.01)
*G16H 50/20* (2018.01)

(52) U.S. Cl.
CPC ....... *G06K 2209/051* (2013.01); *G06N 20/00* (2019.01); *G06T 7/337* (2017.01); *G06T 7/68* (2017.01); *G06T 2207/10081* (2013.01); *G06T 2207/10088* (2013.01); *G06T 2207/10116* (2013.01); *G06T 2207/20076* (2013.01); *G06T 2207/20081* (2013.01); *G06T 2207/30016* (2013.01); *G16H 50/20* (2018.01)

(58) Field of Classification Search
CPC ................ G06N 3/0454; G06N 20/10; G06K 2209/051
See application file for complete search history.

(56) References Cited

U.S. PATENT DOCUMENTS

| | | | |
|---|---|---|---|
| 2015/0065803 A1* | 3/2015 | Douglas | A61B 1/00045 600/200 |
| 2016/0005183 A1* | 1/2016 | Thiagarajan | G06T 7/0012 382/131 |
| 2016/0220166 A1* | 8/2016 | Thornton | A61B 5/7246 |
| 2018/0025255 A1* | 1/2018 | Poole | G06T 7/0014 382/131 |

* cited by examiner

MEDICAL IMAGE PROCESSING APPARATUS, MEDICAL IMAGE PROCESSING METHOD, AND MEDICAL IMAGE PROCESSING PROGRAM

CROSS REFERENCE TO RELATED APPLICATIONS

The present application claims priority under 35 U.S.C. § 119 to Japanese Patent Application No. 2018-172988 filed on Sep. 14, 2018. The above application is hereby expressly incorporated by reference, in its entirety, into the present application.

BACKGROUND

Technical Field

The present invention relates to a medical image processing apparatus, a medical image processing method, and a medical image processing program for determining a disease region in a medical image, such as a brain image.

Related Art

In recent years, advances in medical apparatuses, such as computed tomography (CT) apparatuses and magnetic resonance imaging (MRI) apparatuses, have enabled image diagnosis using high-resolution medical images with higher quality. In particular, in a case where a target part is a brain, a disease region causing a vascular disorder, such as cerebral infarction and cerebral hemorrhage, can be specified by image diagnosis using CT images, MRI images, and the like. Therefore, appropriate treatment based on the specification result is performed. In general, a disease region shows a high CT value compared with the surrounding region on a CT image. For this reason, in image diagnosis, a disease region can be determined by interpreting the presence or absence of a region showing a high CT value compared with the surrounding region.

On the other hand, in a case where the medical image is a non-contrast CT image, in mild subarachnoid hemorrhage or hyperacute cerebral infarction, the contrast between a diseased part and its surrounding part is often unclear. For this reason, in image diagnosis, it is generally performed to interpret whether or not a disease region is present by comparing symmetrical regions of the brain in the medical image.

Various methods for detecting a disease region by comparing such symmetrical regions have been proposed. For example, JP2018-011958A proposes a method of determining the presence or absence of a disease region using a discriminator subjected to machine learning with a combination of left and right symmetrical regions in a medical image as an input.

However, the symmetry axis of the brain included in the medical image may not necessarily be perpendicular to the medical image. In addition, the shape of the brain may differ between the left and right brains. For this reason, the brain included in the medical image may not be exactly symmetrical. Here, in the method described in JP2018-011958A, the medical image itself is input to the discriminator. Therefore, in the method described in JP2018-011958A, although the symmetrical regions of the brain are compared, it is difficult to accurately determine a disease region in a brain image including a brain that is not exactly symmetrical with respect to the symmetry axis.

SUMMARY OF THE INVENTION

The invention has been made in view of the above circumstances, and it is an object of the invention to accurately determine a disease region in a medical image including an axisymmetric structure, such as a brain.

A medical image processing apparatus according to the invention comprises a determination processing unit that determines a disease region in a medical image including an axisymmetric structure. The determination processing unit has: a first determination section that generates a feature amount map of the medical image from the medical image; a second determination section that inverts the feature amount map with reference to a symmetry axis of the feature amount map to generate an inverted feature amount map; and a third determination section that superimposes the feature amount map and the inverted feature amount map on each other and determines the disease region in the medical image using the feature amount map and the inverted feature amount map superimposed on each other.

The "axisymmetric structure" includes not only one structure that is itself axisymmetric on a medical image but also a pair or a plurality of pairs of structures present at axisymmetric positions on a medical image. For example, the brain basically (that is, anatomically) has an axisymmetric shape and accordingly, is assumed to be present axisymmetrically. However, the brain is not exactly axisymmetrical, and the left and right brains may differ in size and shape. The kidneys are also present in an anatomically axisymmetric pair, but the sizes and shapes of the left and right kidneys may be different. For this reason, the "axisymmetric structure" includes not only a structure having a completely symmetrical pair but also a structure that is approximately axisymmetrical and a structure that is assumed to be axisymmetric ally present.

"Determination" may be any of determining the position of a disease region in a medical image and determining the presence or absence of a disease region in a medical image.

In the medical image processing apparatus according to the invention, each of the first determination section, the second determination section, and the third determination section may be a neural network having at least one processing layer.

In the medical image processing apparatus according to the invention, the medical image may be a CT image of a brain, and the disease region may be a disease region within the brain.

In the medical image processing apparatus according to the invention, the disease region may be a bleeding region or an infarct region.

The medical image processing apparatus according to the invention may further comprise a display controller that displays the medical image in which the disease region is determined on a display unit.

A medical image processing method according to the invention is a medical image processing method for determining a disease region in a medical image including an axisymmetric structure with a determination processing unit. The medical image processing method comprises: generating a feature amount map of the medical image from the medical image; inverting the feature amount map with reference to a symmetry axis of the feature amount map to generate an inverted feature amount map; and superimposing the feature amount map and the inverted feature amount map on each other and determining the disease region in the medical image using the feature amount map and the inverted feature amount map superimposed on each other.

A medical image processing program according to the invention is a medical image processing program causing a computer to execute processing for determining a disease region in a medical image including an axisymmetric structure. The medical image processing program causes the computer to execute: a step of generating a feature amount map of the medical image from the medical image; a step of inverting the feature amount map with reference to a symmetry axis of the feature amount map to generate an inverted feature amount map; and a step of superimposing the feature amount map and the inverted feature amount map on each other and determining the disease region in the medical image using the feature amount map and the inverted feature amount map superimposed on each other.

Another medical image processing apparatus according to the invention comprises: a memory that stores commands to be executed by a computer; and a processor configured to execute the stored commands. The processor executes, as processing for determining a disease region in a medical image including an axisymmetric structure, processing for generating a feature amount map of the medical image from the medical image, inverting the feature amount map with reference to a symmetry axis of the feature amount map to generate an inverted feature amount map, and superimposing the feature amount map and the inverted feature amount map on each other and determining the disease region in the medical image using the feature amount map and the inverted feature amount map superimposed on each other.

According to the invention, it is possible to determine a disease region more accurately.

DETAILED DESCRIPTION

Figure 1:
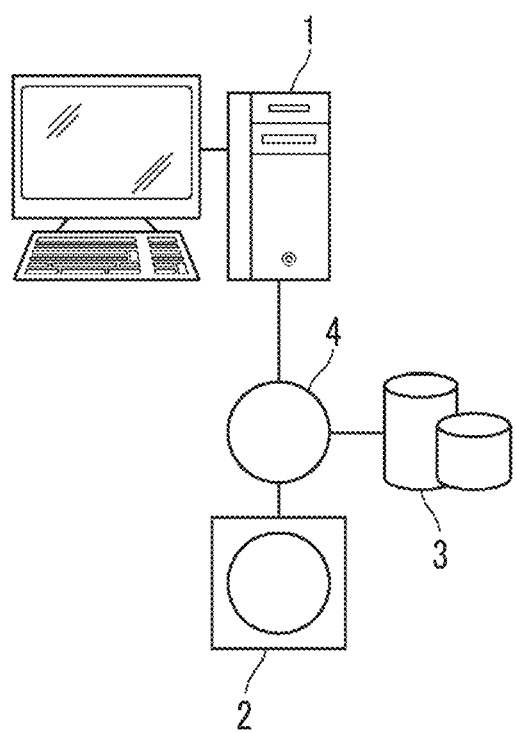
FIG. 1 is a hardware configuration diagram showing an outline of a diagnostic support system to which a medical image processing apparatus according to an embodiment of the invention is applied.

Hereinafter, an embodiment of the invention will be described with reference to the diagrams. FIG. 1 is a hardware configuration diagram showing the outline of a diagnostic support system to which a medical image processing apparatus according to an embodiment of the invention is applied. As shown in FIG. 1, in the diagnostic support system, a medical image processing apparatus 1 according to the present embodiment, a three-dimensional image capturing apparatus 2, and an image storage server 3 are communicably connected to each other through a network 4.

The three-dimensional image capturing apparatus 2 is an apparatus that generates a three-dimensional image showing a diagnostic target part of a subject by imaging the diagnostic target part. Specifically, the three-dimensional image capturing apparatus 2 is a CT apparatus, an MRI apparatus, a positron emission tomography (PET) apparatus, or the like. The three-dimensional image generated by the three-dimensional image capturing apparatus 2 is transmitted to the image storage server 3 and stored therein. In the present embodiment, a diagnostic target part of a patient who is a subject is a brain, the three-dimensional image capturing apparatus 2 is a CT apparatus, and a CT image of the head including the brain of the subject is generated as a three-dimensional brain image B0.

The image storage server 3 is a computer that stores and manages various kinds of data, and comprises a large-capacity external storage device and software for database management. The image storage server 3 communicates with other devices through the wired or wireless network 4 to transmit and receive image data or the like. Specifically, the image storage server 3 acquires various kinds of data including image data of the brain image B0, which is generated by the three-dimensional image capturing apparatus 2, through the network, and stores the acquired data in a recording medium, such as a large-capacity external storage device, to manage the acquired data. The storage format of image data and the communication between devices through the network 4 are based on a protocol, such as a digital imaging and communication in medicine (DICOM).

The medical image processing apparatus 1 is realized by installing a medical image processing program of the invention on one computer. The computer may be a workstation or a personal computer that is directly operated by a doctor who performs diagnosis, or may be a server computer connected to these through a network. The medical image processing program is distributed in a state in which the medical image processing program is recorded on a recording medium, such as a digital versatile disc (DVD) or a compact disc read only memory (CD-ROM), and is installed onto the computer from the recording medium. Alternatively, the medical image processing program is stored in a storage device of a server computer connected to the network or in a network storage so as to be accessible from the outside, and is downloaded and installed onto a computer used by a doctor as necessary.

Figure 2:
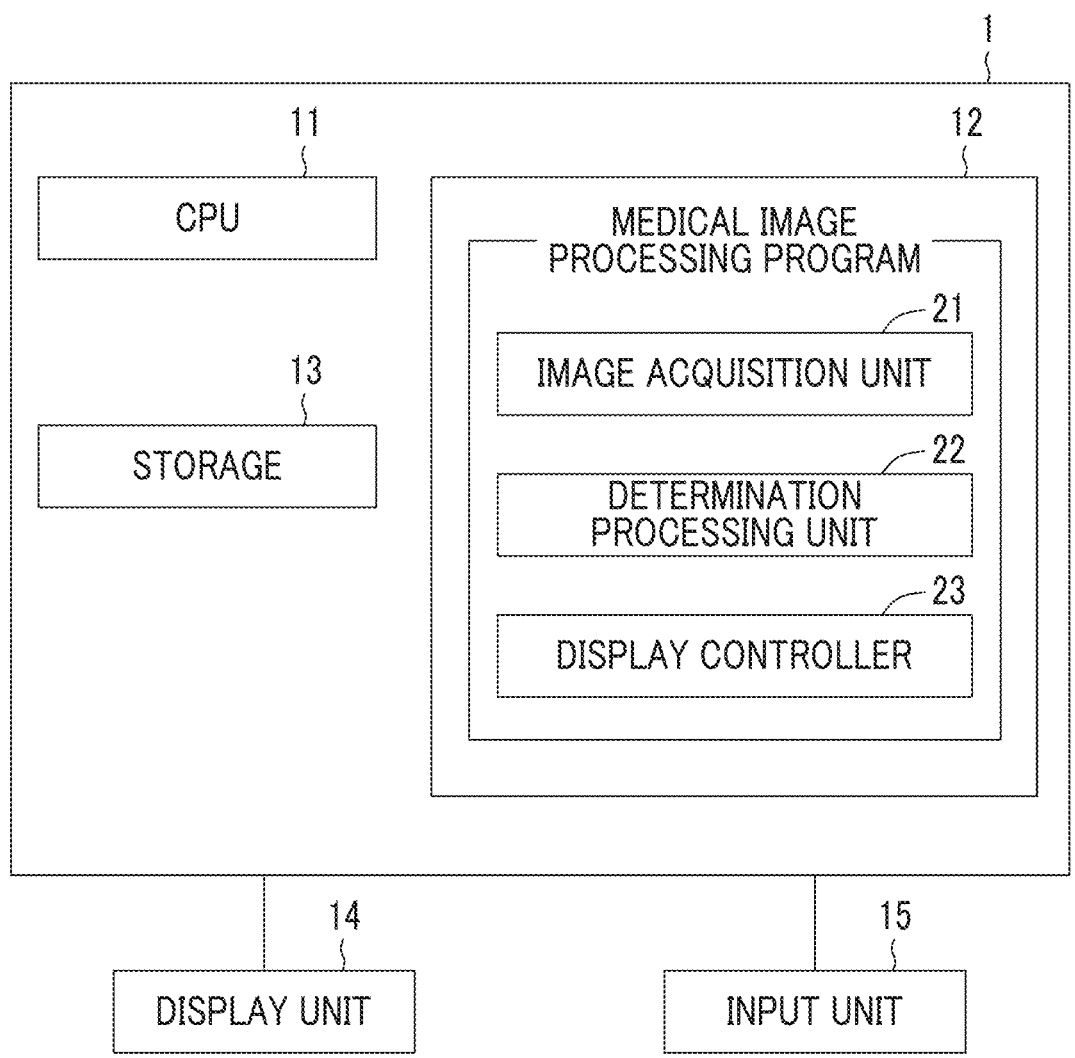
FIG. 2 is a diagram showing the schematic configuration of a medical image processing apparatus according to the embodiment of the invention.

FIG. 2 is a diagram showing the schematic configuration of a medical image processing apparatus realized by installing a medical image processing program on a computer. As shown in FIG. 2, the medical image processing apparatus 1 comprises a central processing unit (CPU) 11, a memory 12, and a storage 13 as the configuration of a standard workstation. A display unit 14, such as a liquid crystal display, and an input unit 15, such as a keyboard and a mouse, are connected to the medical image processing apparatus 1.

The storage 13 includes a hard disk drive and the like, and stores the brain image of the subject and various kinds of information including information necessary for processing, which are acquired from the image storage server 3 through the network 4.

A medical image processing program is stored in the memory 12. As processing to be executed by the CPU 11, the medical image processing program defines image acquisition processing for acquiring the brain image B0 of the subject, determination processing for determining a disease region included in the brain image B0, and display control processing for displaying the determined disease region on the display unit 14.

Then, the CPU 11 executes these processes according to the program, so that the computer functions as an image acquisition unit 21, a determination processing unit 22, and a display controller 23.

The image acquisition unit 21 acquires the brain image B0 of the brain of the subject from the image storage server 3. In a case where the brain image B0 is already stored in the storage 13, the image acquisition unit 21 may acquire the brain image B0 from the storage 13.

The determination processing unit 22 determines a disease region in the brain image B0. In the present embodiment, it is assumed that the disease region is a bleeding region. In the present embodiment, it is assumed that the determination processing unit 22 is a convolutional neural network (hereinafter, referred to as a CNN), which is one of multilayer neural networks in which a plurality of processing layers are hierarchically connected and deep learning is performed.

Figure 3:
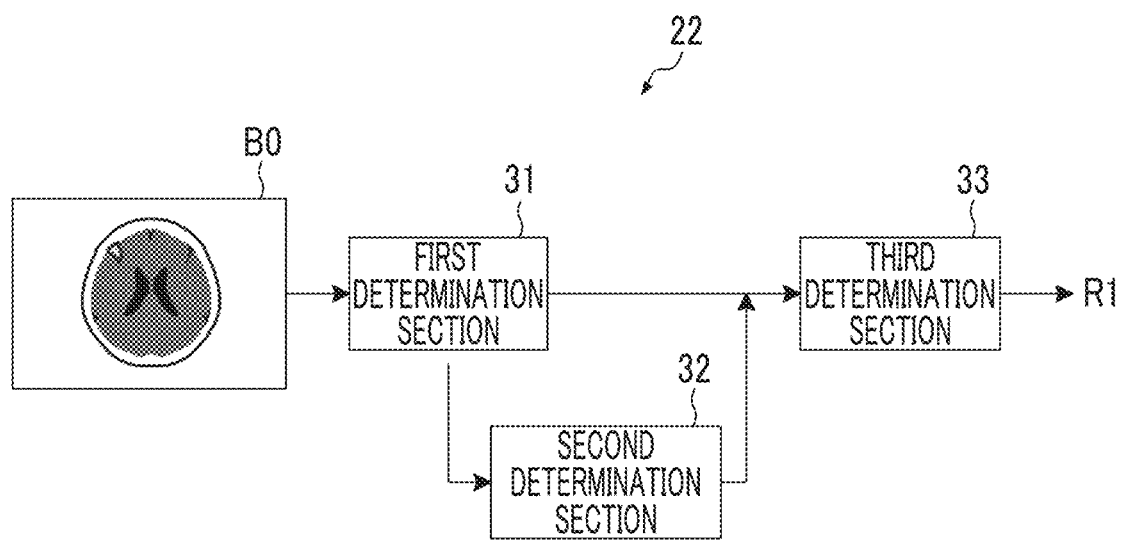
FIG. 3 is a schematic diagram showing the configuration of a determination processing unit in the present embodiment.

FIG. 3 is a schematic diagram showing the configuration of a determination processing unit in the present embodiment. As shown in FIG. 3, the determination processing unit 22 comprises a first determination section 31 that generates a feature amount map of the brain image B0 from the brain image B0, a second determination section 32 that inverts the feature amount map with reference to a symmetry axis to generate an inverted feature amount map, and a third determination section 33 that superimposes the feature amount map and the inverted feature amount map on each other and determines a bleeding region in the brain image B0 using the feature amount map and the inverted feature amount map superimposed on each other.

Each of the first determination section 31, the second determination section 32, and the third determination section 33 is a CNN, and has at least one processing layer. The first processing layer of the first determination section 31 is an input layer of the CNN that configures the determination processing unit 22, and the last processing layer of the third determination section 33 is an output layer.

Processing layers included in the first determination section 31, the second determination section 32, and the third determination section 33 include at least one of a convolution layer or a pooling layer. The convolution layer performs convolution processing using various kernels on an input image, and outputs a feature amount map including feature amount data obtained by the convolution processing. The kernel has an n×n pixel size (for example, n=3), and a weighting is set for each element. Specifically, a weighting such as a differential filter for emphasizing an edge of a two-dimensional image, such as the brain image B0 or a feature amount map, is set. The convolution layer applies the kernel to the entire brain image B0 or the entire feature amount map while shifting the target pixel of the kernel. In addition, the convolution layer applies an activation function, such as a sigmoid function, to the convoluted value and outputs a feature amount map.

The pooling layer reduces the data amount of the feature amount map by pooling the feature amount map output from the convolution layer, and outputs a feature amount map whose data amount has been reduced.

In the present embodiment, the first determination section 31, the second determination section 32, and the third determination section 33 are learned so as to output a determination result R1, which indicates whether or not each pixel of the input brain image is a bleeding region, using a number of brain images including a bleeding region as teacher data. In a case where the brain image B0 is input to the determination processing unit 22, in a plurality of processing layers of the first determination section 31, the second determination section 32, and the third determination section 33, a feature amount map output from the processing layer of the previous stage is sequentially input to the processing layer of the next stage, and the determination result R1 of the bleeding region in the brain image B0 is output.

Figure 4:
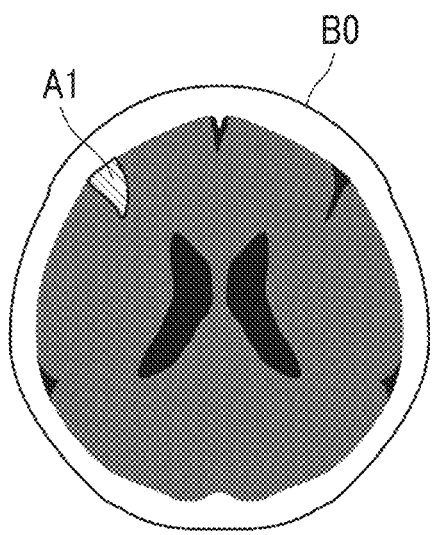
FIG. 4 is a diagram showing a brain image including a bleeding region.
Figure 5:
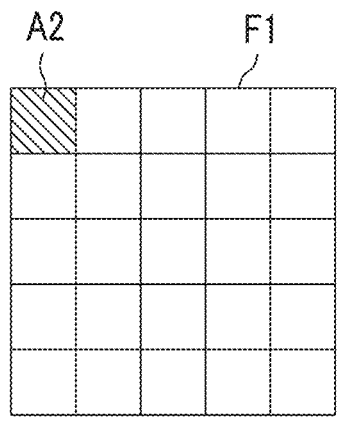
FIG. 5 is a diagram showing a feature amount map.

Here, the first determination section 31 includes a plurality of processing layers, and outputs a feature amount map in each processing layer. Here, since the feature amount map is generated by performing at least one of pooling or convolution processing using a kernel on the brain image B0, the feature amount map has a resolution lower than the brain image B0. FIG. 4 is a diagram showing a brain image. As shown in FIG. 4, the brain image B0 includes a bleeding region A1 in the right brain. In the brain image B0, the left side of the image is the right brain, and the right side of the image is the left brain. Here, it is assumed that the resolution of the brain image B0 is, for example, 1920×1920 pixels. FIG. 5 is a diagram showing an example of the feature amount map output from the first determination section 31. In FIG. 5, in order to simplify the description, the resolution of a feature amount map F1 is set to 5×5 pixels in FIG. 5. However, the invention is not limited thereto. As shown in FIG. 5, the resolution of the feature amount map F1 output from the first determination section 31 is 5×5 pixels, and a feature A2 corresponding to the bleeding region A1 of the brain image B0 shown in FIG. 4 is included in the upper left pixel.

Figure 6:
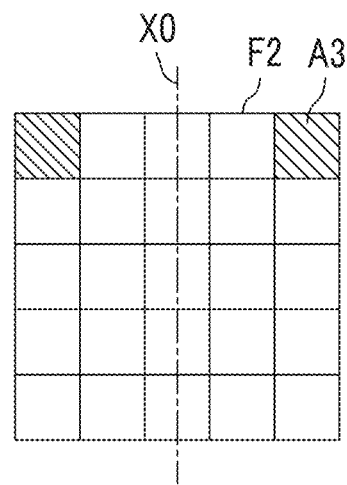
FIG. 6 is a diagram showing an inverted feature amount map.

The second determination section 32 generates an inverted feature amount map F2 by inverting the feature amount map F1 output from the first determination section 31 with reference to the symmetry axis. To this end, the processing layer of the second determination section 32 performs convolution processing for inverting the feature amount map F1 with reference to the symmetry axis. FIG. 6 is a diagram showing an inverted feature amount map. As shown in FIG. 6, the inverted feature amount map F2 is generated by horizontally inverting the feature amount map F1 shown in FIG. 5 with reference to the symmetry axis X0. For this reason, the feature A2 of the right brain present at the upper left of the feature amount map F1 is present as a feature A3 at the upper right of the inverted feature amount map F2. In addition, as long as the second determination section 32 can generate the inverted feature amount map F2 from the feature amount map F1, the second determination section 32 may have only one processing layer or may have a plurality of processing layers.

Figure 7:
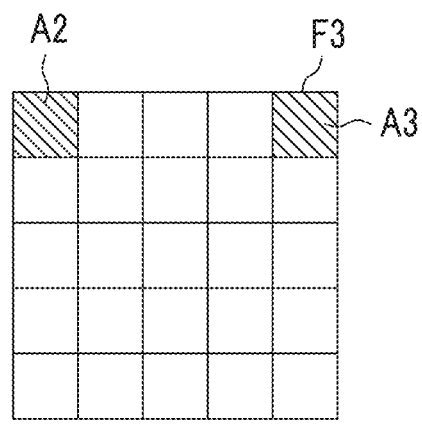
FIG. 7 is a diagram showing a superposition map.

The third determination section 33 includes a plurality of processing layers, and generates a superposition map by superimposing the feature amount map F1 output from the first determination section 31 and the inverted feature amount map F2 output from the second determination section 32 in the first processing layer. FIG. 7 is a diagram showing a superposition map. The third determination section 33 determines a bleeding region in the brain image B0 based on a superposition map F3 in processing layers subsequent to the first processing layer. Here, the front stage of the third determination section 33 performs processing for specifying a bleeding region without changing the size of the superposition map based on the superposition map, and the rear stage of the third determination section 33 performs processing for classifying pixels in the brain image B0 into bleeding regions and pixels other than the bleeding regions while increasing the resolution of the feature amount map, in which the bleeding region is specified, so as to become the resolution of the brain image B0. As a result, the determination result R1 of the bleeding region for each pixel in the brain image B0 is output from the third determination section 33.

Figure 8:
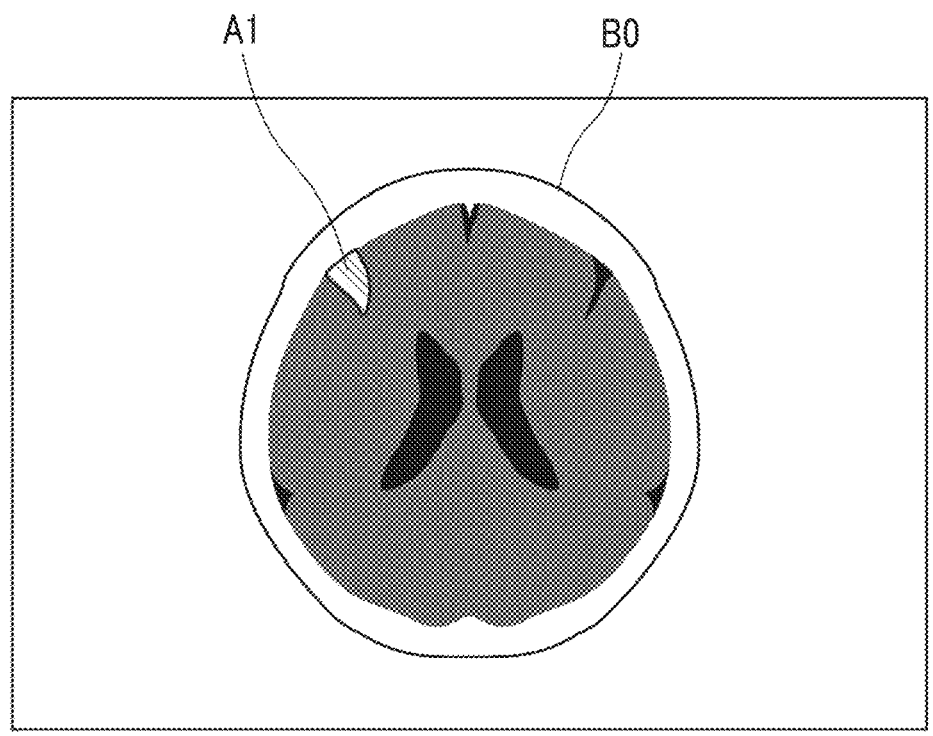
FIG. 8 is a diagram showing a brain image in which a bleeding region is specified.

The display controller 23 displays a brain image, in which the bleeding region is determined, on the display unit 14. FIG. 8 is a diagram showing a displayed brain image. In addition, FIG. 8 shows a slice image of one tomographic plane of the brain image B0. As shown in FIG. 8, the bleeding region A1 determined in the brain image B0 is highlighted and displayed. For the highlight, any method can be used, such as surrounding the bleeding region A1 with a line, giving a specific color to the bleeding region A1, and giving an arrow to the bleeding region A1.

Figure 9:
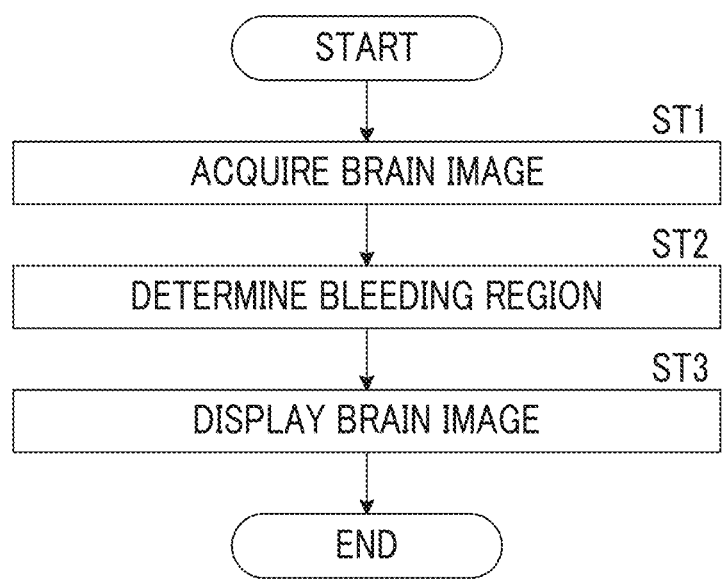
FIG. 9 is a flowchart showing the process performed in the present embodiment.

Next, a process performed in the present embodiment will be described. FIG. 9 is a flowchart showing the process performed in the present embodiment. First, the image acquisition unit 21 acquires the brain image B0 of a subject (step ST1). Then, the determination processing unit 22 determines a bleeding region in the brain image B0 (step ST2), the display controller 23 displays the brain image B0, in which the bleeding region is determined, on the display unit 14 (step ST3), and the process ends.

Figure 10:
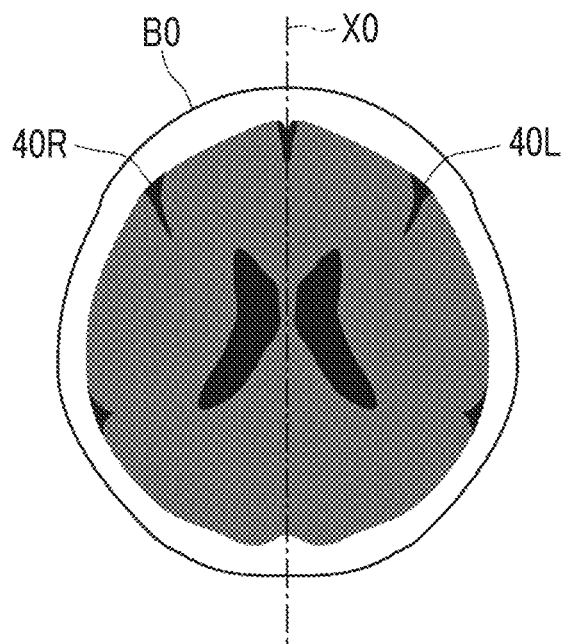
FIG. 10 is a diagram showing a brain image.

Here, the brain included in the brain image B0 is basically an axisymmetric structure with respect to the symmetry axis X0 as shown in FIG. 10. In a CT image, the cerebral sulcus and the cerebral ventricle are high-density (high-brightness) regions. Accordingly, in a normal brain image, the cerebral sulcus and the cerebral ventricle are present symmetrically with respect to the symmetry axis X0. In the brain image B0 shown in FIG. 10, a cerebral sulcus 40L of the left brain and a cerebral sulcus 40R of the right brain can be checked.

Figure 11:
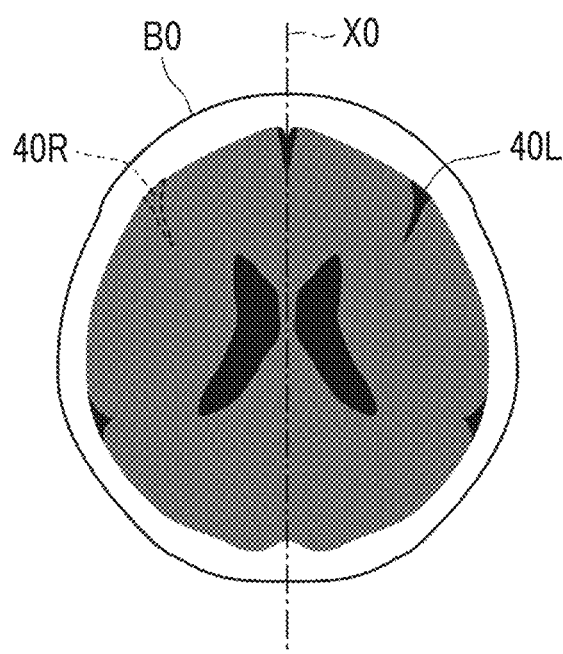
FIG. 11 is a diagram showing a brain image in which a bleeding region is present.

On the other hand, in a case where there is intracerebral hemorrhage, blood flows into the cerebral sulcus and the cerebral ventricle. As a result, the cerebral sulcus and the cerebral ventricle into which blood flows have a concentration similar to that of the cerebral parenchyma. Here, in a case where intracerebral hemorrhage occurs, it is extremely rare that hemorrhage occurs in both the left and right brains. For example, in a case where intracerebral hemorrhage occurs in the cerebral sulcus 40R of the right brain, it is rare that intracerebral hemorrhage occurs in the cerebral sulcus 40L of the left brain. In such a situation, as shown in FIG. 11, the cerebral sulcus 40L of the left brain can be checked in the brain image B0, but the cerebral sulcus 40R of the right brain is difficult to check since the cerebral sulcus 40R of the right brain has a concentration similar to that of the cerebral parenchyma. For this reason, a bleeding region can be specified by comparing the left and right brains and checking the difference between the concentration of the cerebral sulcus 40L of the left brain and the concentration of the cerebral sulcus 40R of the right brain.

However, in the brain image, the symmetry axis of the brain may not necessarily be perpendicular to the brain image. In addition, the shape of the brain may differ between the left and right brains. For this reason, the brain included in the brain image may not be exactly symmetrical. In the method described in JP2018-011958A, the medical image itself is input to a discriminator. Therefore, in the method described in JP2018-011958A, although the symmetrical regions of the brain are compared with each other, it is difficult to accurately determine a disease region in a brain image including a brain that is not exactly symmetrical with respect to the symmetry axis.

In the present embodiment, the second determination section 32 inverts the feature amount map F1 generated by the first determination section 31 to generate the inverted feature amount map F2, and the third determination section 33 determines a bleeding region using the inverted feature amount map F2. Since the feature amount map F1 has lower resolution than the brain image B0, the deviation of symmetry with respect to the symmetry axis is absorbed, and the bleeding region is determined. Therefore, according to the present embodiment, even in the case of a brain image including a brain that is not exactly symmetrical with respect to the symmetry axis, it is possible to accurately determine a bleeding region.

Although the feature amount map F1 output from the first determination section 31 is input to the second determination section 32 in the above embodiment, the feature amount map F1 input to the second determination section 32 may be output from the processing layer in the middle of the first determination section 31.

Although the bleeding region is used as a disease region in the above embodiment, the invention is not limited thereto, and an infarct region may be used as disease region.

In the above embodiment, the determination processing unit 22 outputs the determination result R1 in which pixels in the brain image B0 are classified into bleeding regions and pixels other than the bleeding regions. However, the presence or absence of a bleeding region in the brain image B0 may be output as the determination result R1. In this case, the first determination section 31, the second determination section 32, and the third determination section 33 are learned so as to output the presence or absence of a disease region as the determination result R1 in a case where the brain image B0 is input.

In the above embodiment, the CT image is used as the brain image B0. However, the invention is not limited thereto, and other medical images, such as an MRI image and a PET image, may be used.

In the above embodiment, the brain image is used as a medical image. However, the invention is not limited thereto. For example, the invention can also be applied to a case of determining a disease region in a medical image including a pair or a plurality of pairs of axisymmetric structures, such as lungs, kidneys, eyes, and ears.

In the above embodiment, the convolutional neural network (CNN) is used as the first determination section 31, the second determination section 32, and the third determination section 33. However, the invention is not limited thereto. As long as a disease region can be determined, a support vector machine (SVM), a deep neural network (DNN), a recurrent neural network (RNN), and the like can be used. The first determination section 31, the second determination section 32, and the third determination section 33 may not be the same type of neural network. For example, the first determination section 31 and the second determination section 32 may be convolutional neural networks, and the third determination section 33 may be a recurrent neural network.

In the embodiment described above, for example, various processors shown below can be used as the hardware structures of processing units for executing various kinds of processing, such as the image acquisition unit 21, the determination processing unit 22, and the display controller 23. The various processors include not only the above-described CPU, which is a general-purpose processor that executes software (program) to function as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, as the hardware structure of these various processors, it is possible to use an electrical circuit (circuitry) in which circuit elements, such as semiconductor elements, are combined.

What is claimed is:

1. A medical image processing apparatus, comprising:
a central processing unit (CPU) to determine a disease region in a medical image including an axisymmetric structure,
wherein the CPU has:
a first determination section, to be executed by the CPU, to generate a feature amount map of the medical image from the medical image;
a second determination section, to be executed by the CPU, to invert the feature amount map with reference to a symmetry axis of the feature amount map to generate an inverted feature amount map; and
a third determination section, to be executed by the CPU, to superimpose the feature amount map and the inverted feature amount map on each other and to determine the disease region in the medical image using the feature amount map and the inverted feature amount map superimposed on each other, and
wherein the feature amount map has lower resolution than the medical image.

2. The medical image processing apparatus according to claim 1,
wherein each of the first determination section, the second determination section, and the third determination section is a neural network having at least one processing layer.

3. The medical image processing apparatus according to claim 1,
wherein the medical image is a CT image of a brain, and the disease region is a disease region within the brain.

4. The medical image processing apparatus according to claim 3,
wherein the disease region is a bleeding region or an infarct region.

5. The medical image processing apparatus according to claim 1, further comprising:
a display controller to display the medical image in which the disease region is determined on a display unit.

6. A medical image processing method for determining a disease region in a medical image including an axisymmetric structure with a determination processing unit, the method comprising:
generating a feature amount map of the medical image from the medical image;
inverting the feature amount map with reference to a symmetry axis of the feature amount map to generate an inverted feature amount map; and
superimposing the feature amount map and the inverted feature amount map on each other and determining the disease region in the medical image using the feature amount map and the inverted feature amount map superimposed on each other,
wherein the feature amount map has lower resolution than the medical image.

7. A non-transitory computer-readable storage medium that stores a medical image processing program causing a computer to execute processing for determining a disease region in a medical image including an axisymmetric structure, the program causing the computer to execute:
a step of generating a feature amount map of the medical image from the medical image;
a step of inverting the feature amount map with reference to a symmetry axis of the feature amount map to generate an inverted feature amount map; and
a step of superimposing the feature amount map and the inverted feature amount map on each other and determining the disease region in the medical image using the feature amount map and the inverted feature amount map superimposed on each other,
wherein the feature amount map has lower resolution than the medical image.

* * * * *